(12) United States Patent
Sadler et al.

(10) Patent No.: US 6,371,370 B2
(45) Date of Patent: *Apr. 16, 2002

(54) APPARATUS AND METHOD FOR SCANNING A SURFACE

(75) Inventors: John W. Sadler, Belmont; Andreas N. Dorsel, Menlo Park; Kenneth L. Staton, San Carlos, all of CA (US)

(73) Assignee: Agilent Technologies, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,654

(22) Filed: May 24, 1999

(51) Int. Cl.[7] .................................................. G06K 7/14
(52) U.S. Cl. .................. 235/454; 235/462.23; 235/470; 369/44.25; 369/44.34
(58) Field of Search .......................... 235/454, 462.23, 235/462.33, 470; 369/44.25, 44.26, 44.34, 52, 54

(56) References Cited

U.S. PATENT DOCUMENTS

| | | | | |
|---|---|---|---|---|
| 4,888,756 A | * | 12/1989 | Shikichi et al. ................. 369/45 |
| 4,963,718 A | * | 10/1990 | Hoshizaki et al. ...... 235/462.01 |
| 5,122,644 A | * | 6/1992 | Hasegawa et al. ...... 235/462.01 |
| 5,315,321 A | * | 5/1994 | Peled et al. .................. 346/108 |
| 5,616,909 A | * | 4/1997 | Arackellian ............ 235/472.01 |
| 5,896,353 A | * | 4/1999 | Naohara ................... 369/44.25 |
| 6,225,625 B1 | * | 5/2001 | Pirrung et al. .............. 250/302 |

* cited by examiner

*Primary Examiner*—Karl D. Frech
*Assistant Examiner*—Daniel St. Cyr

(57) ABSTRACT

Apparatus and method for scanning a surface. An optical system generates a light beam to illuminate a surface. A carrier supports the surface for reciprocating motion with respect to the light beam to form one axis of a raster. A propulsion system moves the carrier at a substantially constant speed and a position sensor provides an output signal representing the surface position with respect to the light beam. A control system responsive to the output signal modulates a sample period reciprocally to carrier speed to achieve substantially constant scan length per sample and to control data acquisition timing.

15 Claims, 1 Drawing Sheet

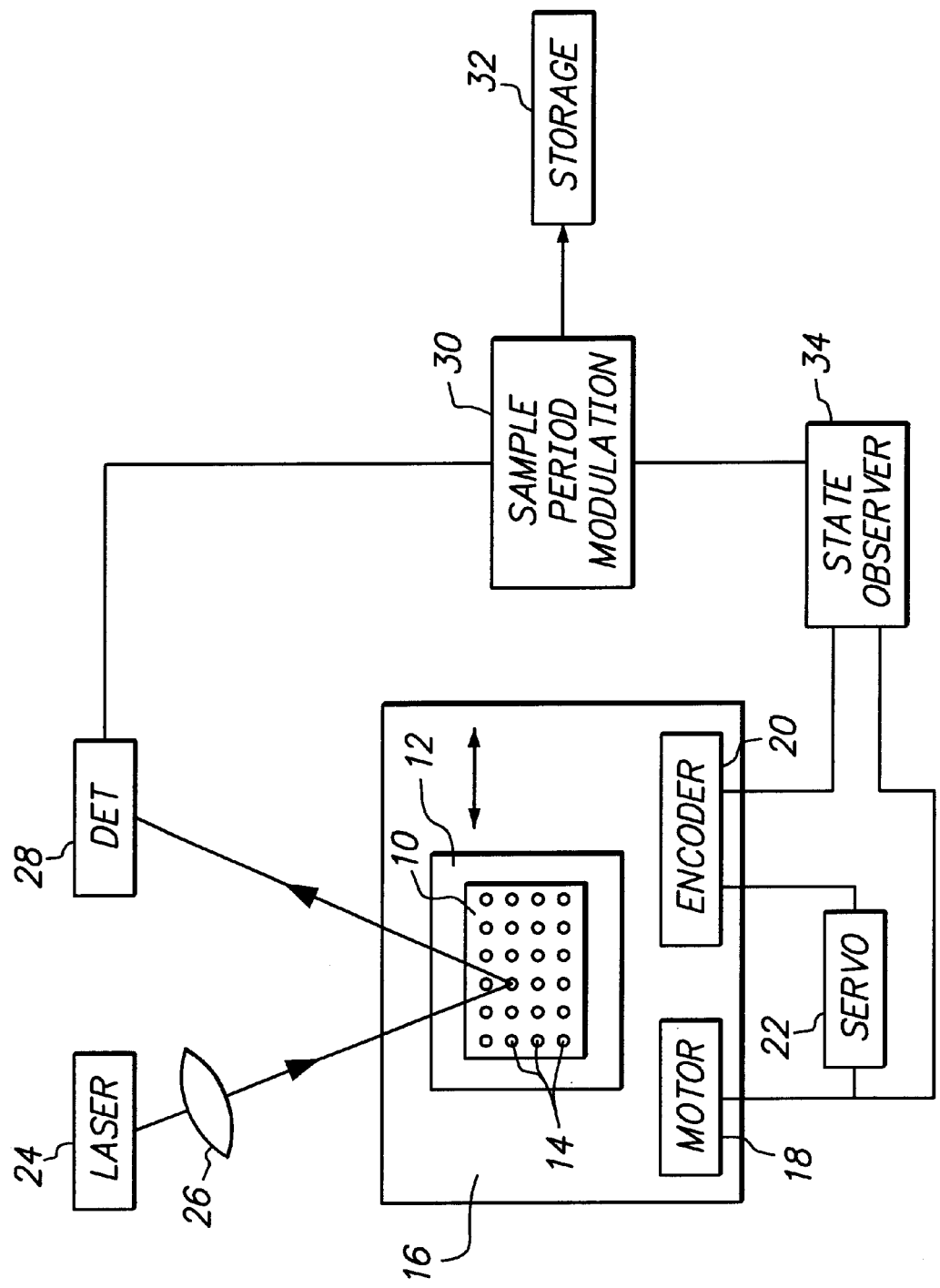

APPARATUS AND METHOD FOR SCANNING A SURFACE

BACKGROUND OF THE INVENTION

This invention relates to scanning a surface and more particularly to such a system which can achieve constant scan length per data sample.

Scanning imaging systems form a map of some characteristic of a surface of interest by exposing the surface to light and measuring a response from the surface. A focused beam of light is moved in a deliberate and repeatable pattern with respect to the surface. The response is generally time-correlated to the position of the scanning beam in order to form a final map of the property with respect to a location on the surface. In most situations, it is important to be able to infer the position of the surface represented by each pixel and to be able to guarantee that the pixel spacing is uniform within some tolerance dictated by the size of the features being scanned.

Relative motion between the light beam and the surface can be achieved by maintaining the surface stationary and moving the beam or, alternatively, keeping the beam stationary while moving the surface. A high performance (high numerical aperture) optical system of reasonable cost, often has a scanner in which a surface moves while the illuminating beam stays in a constant position relative to the beam optics. Such an arrangement results in the desirable property of high numerical aperture. Alternatively, the surface may remain fixed with the light beam being moved. The components that position the surface relative to the beam generally exhibit some systematic position errors that are a function of position or time. These errors degrade the quality of the final map of the desired property with respect to a location on the surface.

The present invention has particular application to gene chips which contain arrays of short DNA chains in an array of sequences bound to a substrate (usually glass). The chip is indexed so that the particular DNA sequence bound in any area is known. A region having a homogeneous composition is referred to as a "feature." The DNA chips can be incubated with a solution containing RNA or DNA bound to a fluorescent tag, allowing the binding of RNA to individual features. Such systems can be used for the determination of both genotype and gene expression levels.

If fluorescence is observed in a particular region, binding has occurred and a DNA sequence is identified by consulting the index of DNA positions on the chip. The present invention is particularly useful in this context. As will be discussed below, the present invention sets forth a methodology for measuring and compensating position errors which may be a function of position or time to an arbitrary level of linearity.

SUMMARY OF THE INVENTION

In one aspect, the apparatus for scanning a surface includes an optical system to generate a light beam and to deliver the beam to a surface. A carrier supports the surface and is mounted for reciprocating motion with respect to the light beam to form one axis of a raster. Of course, the surface may be fixed with the optics arranged to sweep the light beam. A propulsion system generates forces for moving the carrier and a position sensor generates an output signal representing the surface position with respect to the light beam. A servo system responsive to the output signal is provided for commanding the propulsion system to move the carrier at a substantially constant speed in a scanning region. A control system responsive to the output signal is provided to modulate a sample period reciprocally to carrier speed to achieve substantially constant scan length per sample and to control data acquisition timing.

In one embodiment, the position sensor, which is monotonic and repeatable, is selected from a group including a counting position encoder, optical encoder, magnetic encoder, capacitive encoder, laser interferometer, an LVDT or reflected optical triangulation device. The propulsion system may include a motor, voice coil, a galvanometer, a gas jet or a graphite piston in a glass cylinder powered by a ts gas or liquid. A state observer may be provided to generate an estimate of carrier speed for use by the sample period modulation system. A system may also be provided for compensating for variable integral illumination per sample. One such technique includes scaling the amplitude of a measured signal by a function of a ratio of an actual sample period to a nominal sample period.

In yet another embodiment of the invention, data acquisition timing is controlled by a state machine that triggers data acquisition when a selected number of new counts in a correct direction has occurred. The inputs to the state machine may be quadrature decoded direction and quadrature decoded count information. The state machine is programmed so that new counts in the correct direction are detected by counting backwards quadrature state changes and incrementing a trigger counter on quadrature state changes only when a backwards counter is zero.

In yet another embodiment, data acquisition timing is triggered by the first equivalence of an actual position value and a selected trigger position in which a counter is rapidly incremented, for example, ten times.

The approach of the present invention permits a highly linear scan (in the sense that the servo system actively regulates the sample period to give constant pixel size) even in the presence of disturbances such as friction and vibration.

BRIEF DESCRIPTION OF THE DRAWINGS

FIG. 1 is a schematic view of the system of the invention.

DESCRIPTION OF THE PREFERRED EMBODIMENT

With reference to FIG. 1 a "gene chip" or plate 10 is mounted on a carrier 12. The plate 10 includes an array 14 of biochemical specimens or test spots on its surface. The biochemical specimens may be DNA chains bound to the plate 10 which may be glass. Of course, the scanning system of the invention has application to scanning systems apart from scanning gene chips.

The carrier 12 preferably has a low mass and is mounted for reciprocating movement with respect to a support 16. The carrier 12 and the support 16 may form an air bearing allowing low friction motion of the carrier 12 with respect to the support 16. In the embodiment illustrated in FIG. 1, the carrier 12 is moved by a motor 18 such as a linear motor having one portion fixed on the support 16 and the other portion on the carrier 12. Alternatively, the carrier 12 may be moved relative to the support 16 with voice coils, galvanometers, gas jets or graphite pistons in glass cylinders. Obviously one could move the lens while holding the substrate carrier fixed.

The position of the carrier 12 with respect to the underlying support 16 (and also with respect to a collimated light beam described below) is measured by an encoder 20. It is preferred that the encoder 20 be a non-contact position sensing device (in order to reduce friction) to measure position of the carrier 12 with respect to the support 16 as the carrier 12 moves. Example non-contact sensors include optical, magnetic, or capacitive encoders, laser interferometers, LVDT's or reflective optical triangulation. Counting position encoders such as optical and non-optical grating encoders allow a particularly simple implementation. As another example, one could measure the position of a laser spot on the chip carrier with a CCD wherein the laser projects a line at an angle to the axis of motion.

An output of the encoder 20 becomes an input to a servo system 22 whose output controls the motor 18. The servo system 22 commands the motor 18 to drive the carrier 12 in a reciprocating motion and to maintain a substantially constant speed in a scanning region to be described hereinbelow.

A laser 24 and lens 26 form an exemplary optical system for delivering a focused beam of light onto the gene chip or plate 10. A test spot within the array 14 may fluoresce upon illumination by the focused beam and the fluorescence is detected by a detector 28. A sample period modulation system 30 responds to the speed of the carrier 12 to alter the scanner sample period reciprocally to the speed of the carrier 12 to achieve a constant scan length per sample and to control data acquisition timing. The output of the detector 20 is then stored in storage element 32 which may be part of a digital computer system (not shown). The sample period modulation system 30, such as a digital integrator, responds to position information from the encoder 20. The system 30, in some circumstances, may derive carrier 12 speed by measuring the time interval between sensed position increments from the encoder 20. Alternatively, a state observer 34 may be provided which includes a dynamic model of the carrier-motor-encoder system. The state observer 34 responds to an output from the encoder 20 and to commands to the motor 18 from the servo system 22 to provide an estimate of a state variable such as speed of the carrier 12. This speed is used by the sample period modulation system 30 to modulate the scanner sample period to achieve substantially constant scan length per sample.

In operation, the carrier 12 reciprocates rapidly under the focused light beam from the laser 24. The servo system 22 attempts to maintain a highly constant speed of the carrier 12 in the scanning region, but speed can vary because of disturbances such as friction and vibration. Because speed may vary, actual speed is measured, inferred or estimated and any speed variation serves as an error signal for modulating the sample time period in the system 30. That is, if the speed is too low then the sample period will be increased to assure a constant scan length per sample. Similarly, if the speed of the carrier 12 is too high, the sample period will be reduced to achieve constant scan length per sample. Speed errors can thereby be compensated to an arbitrary level of linearity. Said another way, $T_{SN} \cong T_{S(N-1)} - k\epsilon$ where $T_{SN}$ is the sample period for sample N, $T_{S(N-1)}$ is the sample period for the sample N-1, and $\epsilon$ is the variation or error in speed which, of course, may be a positive or negative value. It is recognized that there is a trade-off in the uniformity of illumination per unit distance as more nearly constant scan length is achieved.

In a particularly simple implementation of the system of the invention, the encoder system 20 is used to control scan speed only to a level at which spatial variations of saturation and/or bleaching of dye molecules in the array 14 are kept below an acceptable limit. Pixel acquisition is then simply synchronized to (triggered by) the encoder 22 output directly and the number of samples averaged within a pixel is kept fixed at a number that can be completed in the shortest expected pixel time.

For realistic conditions, the small gaps in data acquisition will be sufficiently averaged over by the reading spot size being wider than the gaps. A synchronization signal can be derived directly from transitions of a grating encoder (in which case it can be set to one value out of a fixed (infinite) set of ratios relative to the grating period) or it can be derived from the digitized encoder outputs, often allowing further interpolation. For example, with a nominal linear scan speed of b 1m/s, a pixel size of 10 $\mu$m and a gap of 1 $\mu$m (which does hardly degrade S/N for a 5 $\mu$m FWHM spot) a speed variation of 10% would be acceptable if other sources are neglected. Spending half of this margin on, for example, clock frequency drift of the oscillator controlling sample acquisition still allows for a 5% P–V speed variation. (In a typical system, 226 samples would be acquired in 9 $\mu$s at a fixed rate of one sample/40 ns). Alternately, one can accumulate as many pixels as possible during the pixel time and then normalize by either dividing by the number samples (times a scale factor) or by using a look-up table for speeding up this division.

As stated above, modulating the sample period according to the invention to deliver constant pixel size results in variable integral illumination per sample. This effect can be compensated for by scaling the amplitude of the measured signal by a function of the ratio of the actual sample period to a nominal value. In the case of laser excited fluorescent scanning, the function will be proportional to the reciprocal of the sample period only if the fluorescent dye is in its linear region, that is, not saturated or bleaching appreciably. Alternatively, variable integral illumination per sample can be compensated by controlling intensity of the light source. Note that any repeatable and invertible relationship between integral illumination and emission intensity can be used for the basis for a compensating function in the non-linear case. The scaling operation changes noise proportionally to amplitude rather than to the square root of amplitude so that artifacts of the compensation may be noticeable.

In a particularly preferred embodiment, the position sensor or encoder 20 triggers data acquisition at specified positions or position intervals. The sensor output signal is integrated using a digital integrator which may be included in the sample period modulation unit 30 that accumulates signal samples at, for example, a 40 ns rate. The number of samples varies with the velocity of the carrier 12. The data read includes the integrated signal and number of samples (integration time). It is appropriate to use 32 bits, 10 bits for the number of samples and 22 bits for the signal. The signal value is divided by a quantity which is the number of samples divided by a scale factor. The sensed position is compared to a sequence of trigger positions. This comparison is based on a threshold and requires hysteresis (where the output depends on the input and its recent history) to prevent multiple triggers for the same pixel. Defining the amount of hysteresis to use is an issue. If the position sensor were ideal and the motion were always in the direction of scan travel, then no hysteresis is needed. Real systems, however, have vibration and sensor jitter (position that alternates between two values due to the least significant bit's threshold).

Hysteresis defines separate thresholds for high to low and low to high input transitions. We want the output to ignore the input after the threshold is crossed the first time. We also need to be able to change the direction and change the threshold (trigger position).

The position sensor jitter will result in extra pixels being acquired. One solution to this situation is to implement a state machine that triggers data acquisition when the desired number of new counts in the correct direction has occurred. The servo system defines the correct direction for this state machine. Other state machine inputs are the quadrature decoded direction and the quadrature decoded count (that indicates when a quadrature state change occurs). With a 1 $\mu$m encoder resolution and a 10 $\mu$m pixel size, data acquisition is triggered every 10 new encoder counts. New counts in the correct direction are detected by counting backwards quadrature state changes and incrementing a trigger counter on quadrature state changes only when the backwards counter is zero (no backwards state changes have been recorded).

Another way of implementing this scheme is to compare the actual position value to a trigger position and on the first equivalence trigger data acquisition and add 10 to the trigger position. The trigger position can be implemented as a counter that is rapidly incremented 10 times. Ideally, this counter increment occurs before the next encoder (actual position) state change, which is about one microsecond in our system, so the counter must be incremented at a 100 ns (10 mhz) rate.

Note that the encoder triggered data acquisition is registered by an index pulse at each end of a scan line. This index signal is also derived from the sensed position and is also susceptible to multiple transitions unless hysteresis is used. The same position qualification scheme used for the data trigger can be used for the two indices.

Velocity controlled sampling avoids this position comparison. It requires predicting the sample time. The digital integrator must now be told how many samples to take by the servo because the servo and digital integrator are asynchronous and the servo is slower. The prediction is still limited by position sensor jitter if the velocity is derived from the position rather than directly measured. The servo loop runs at 100 microseconds but the data acquisition must run at 10 microseconds (for 10 $\mu$m pixels).

It is intended that all modification and variations of the invention disclosed herein be included within the scope of the appended claims.

What is claimed is:

1. Apparatus for scanning a surface comprising:
    an optical system to generate a light beam and to deliver the beam to a surface;
    a detector for detecting a response of the surface to the light beam;
    a carrier supporting the surface for reciprocating motion with respect to the light beam to form one axis of a raster;
    a propulsion system for moving the carrier;
    a position sensor providing an output signal representing the surface position with respect to the light beam;
    a servo system responsive to the output signal for commanding the propulsion system to move the carrier at a substantially constant speed; and
    a control system responsive to the output signal to modulate a sample period of the detector reciprocally to carrier speed to achieve substantially constant scan length per sample and to control data acquisition timing.

2. The apparatus of claim 1 wherein the position sensor is selected from the group comprising a counting position encoder, optical encoder, magnetic encoder, capacitive encoder, laser interferometer, LVDT, or reflective optical triangulation device.

3. The apparatus of claim 1 wherein the propulsion system comprises a voice coil.

4. The apparatus of claim 1 wherein the propulsion system comprises a galvanometer.

5. The apparatus of claim 1 wherein the propulsion system comprises a gas jet.

6. The apparatus of claim 1 wherein the propulsion system comprises a graphite piston in a glass cylinder powered by a gas or liquid.

7. The apparatus of claim 1 wherein the propulsion system comprises a rotary servo motor.

8. The apparatus of claim 1 further including a state observer responsive to the output signal to generate an estimate of carrier speed.

9. The apparatus of claim 1 further including means for compensating for variable integral illumination per sample.

10. The apparatus of claim 9 wherein the means for compensating comprises scaling amplitude of a measured signal by function of the ratio of an actual sample period to a nominal sample period.

11. The apparatus of claim 1 wherein data acquisition timing is controlled by a state machine that triggers data acquisition when a selected number of new counts in a correct direction has occurred.

12. The apparatus of claim 11 wherein inputs to the state machine are quadrature decoded direction and quadrature decoded count information.

13. The apparatus of claim 11 wherein the state machine is programmed so that new counts in the correct direction are detected by counting backwards quadrature state changes and incrementing a trigger counter on quadrature state changes only when a backwards counter is zero.

14. The apparatus of claim 1 wherein data acquisition timing is triggered by the first equivalence of an actual position value and a selected trigger position.

15. An apparatus for scanning a surface comprising:
    a detector for detecting an optical signal from the surface;
    a carrier supporting the surface, wherein the detector or the carrier moves with respect to the other to form a raster;
    a position sensor providing an output signal representing the relative surface position of the detector; and
    a control system responsive to the output signal to modulate a sample period of the detector reciprocally to raster speed to achieve substantially constant scan length per sample and to control data acquisition timing.

* * * * *